US008642821B2

(12) United States Patent
Layman, Jr. et al.

(10) Patent No.: US 8,642,821 B2
(45) Date of Patent: Feb. 4, 2014

(54) BROMINATION OF TELOMER MIXTURES DERIVED FROM TOLUENE AND STYRENE

(75) Inventors: William J. Layman, Jr., Baton Rouge, LA (US); Charles H. Kolich, Baton Rouge, LA (US); Arthur G. Mack, Prairieville, LA (US); Steven A. Anderson, Baton Rouge, LA (US); Jonathan P. McCarney, Baton Rouge, LA (US); Jorge Morice, Baton Rouge, LA (US); Zhongxin Ge, Baton Rouge, LA (US); Junzuo Wang, Little Rock, AR (US)

(73) Assignee: Albemarle Corporation, Richmond, VA (US)

( * ) Notice: Subject to any disclaimer, the term of this patent is extended or adjusted under 35 U.S.C. 154(b) by 219 days.

(21) Appl. No.: 13/130,101

(22) PCT Filed: Nov. 30, 2009

(86) PCT No.: PCT/US2009/066127
§ 371 (c)(1),
(2), (4) Date: Sep. 13, 2011

(87) PCT Pub. No.: WO2010/065464
PCT Pub. Date: Jun. 10, 2010

(65) Prior Publication Data
US 2011/0224467 A1 Sep. 15, 2011

Related U.S. Application Data

(60) Provisional application No. 61/119,276, filed on Dec. 2, 2008.

(51) Int. Cl.
*C07C 19/00* (2006.01)

(52) U.S. Cl.
USPC ........... 570/254; 570/190; 570/252; 570/253; 525/333.3; 525/356

(58) Field of Classification Search
None
See application file for complete search history.

(56) References Cited

U.S. PATENT DOCUMENTS

| | | | |
|---|---|---|---|
| 2,243,543 A | 5/1941 | ter Horst | |
| 2,757,146 A | 7/1956 | Fawcett | |
| 2,914,489 A | 11/1959 | Hall | |
| 2,954,412 A | 9/1960 | Wulf et al. | |
| 3,221,068 A | 11/1965 | Gorham | |
| 3,372,880 A | 3/1968 | O'Hara | |
| 3,373,135 A | 3/1968 | Jenkner et al. | |
| 3,451,988 A | 6/1969 | Langer, Jr. | |
| 3,458,586 A | 7/1969 | Langer, Jr. | |
| 3,536,679 A | 10/1970 | Langer, Jr. | |
| 3,541,149 A | 11/1970 | Langer, Jr. | |
| 3,594,396 A | 7/1971 | Langer, Jr. | |
| 3,634,548 A | 1/1972 | Harwell et al. | |
| 3,668,263 A | 6/1972 | Morrison et al. | |
| 3,725,368 A | 4/1973 | Morrison et al. | |
| 3,742,077 A | 6/1973 | Kamienski et al. | |
| 3,751,384 A | 8/1973 | Langer, Jr. | |
| 3,751,501 A | 8/1973 | Kamienski et al. | |
| 3,850,882 A | 11/1974 | Underwood et al. | |
| 3,943,195 A | 3/1976 | Naarmann et al. | |
| 4,041,088 A | 8/1977 | Bach et al. | |
| 4,074,032 A * | 2/1978 | Naarmann et al. | 525/357 |
| 4,078,019 A | 3/1978 | Langer, Jr. | |
| 4,107,231 A | 8/1978 | Wurmb et al. | |
| 4,108,921 A | 8/1978 | Langer, Jr. | |
| 4,129,551 A | 12/1978 | Rueter et al. | |
| 4,129,705 A | 12/1978 | de Zarauz | |
| 4,134,938 A | 1/1979 | Langer, Jr. | |
| 4,137,212 A | 1/1979 | Theysohn et al. | |
| 4,143,221 A | 3/1979 | Naarmann et al. | |
| 4,151,223 A | 4/1979 | Neuberg et al. | |
| 4,200,702 A | 4/1980 | Gausepohl et al. | |
| 4,268,705 A | 5/1981 | Palmer | |
| 4,311,818 A | 1/1982 | Sigwalt et al. | |
| 4,360,455 A | 11/1982 | Lindenschmidt et al. | |
| 4,435,312 A | 3/1984 | Lecolier et al. | |
| 4,450,259 A | 5/1984 | Roggero et al. | |
| 4,463,135 A | 7/1984 | Maly | |
| 4,482,677 A | 11/1984 | Teranaka et al. | |
| 4,535,135 A | 8/1985 | Lecolier et al. | |
| 4,636,540 A | 1/1987 | Warfel | |
| 4,701,498 A | 10/1987 | Roggero et al. | |
| 4,734,461 A | 3/1988 | Roggero et al. | |
| 4,753,745 A | 6/1988 | Kostusyk et al. | |
| 4,755,573 A | 7/1988 | Aycock | |

(Continued)

FOREIGN PATENT DOCUMENTS

| | | |
|---|---|---|
| CN | 100369941 C | 2/2008 |
| DE | 1570376 | 7/1969 |
| DE | 1589700 | 7/1970 |
| DE | 2050009 | 5/1971 |
| DE | 2758781 | 7/1979 |
| DE | 19516563 A1 | 11/1996 |
| EP | 0000141 A1 | 1/1979 |
| EP | 0002514 B2 | 6/1979 |
| EP | 0277429 B1 | 8/1988 |
| EP | 0334715 B1 | 9/1989 |

(Continued)

OTHER PUBLICATIONS

CAPLUS Abstract of Morton, M., "Homogeneous anionic polymerization. II. Molecular weight of polystyrene initiated by lithium alkyls", Journal of Polymer Science, 1963, Part A-1, pp. 461-474. 1 page.

CAPLUS Abstract of Narita, T., et al., "Reactivity of butyllithium-MeOCH2CH2OLi System as catalyst for copolymerization of styrene with 1,3-butadiene", Journal of Macromolecular Science, Chemistry, 1970, 4(2), pp. 277-294. 1 page.

(Continued)

*Primary Examiner* — Sudhakar Katakam
(74) *Attorney, Agent, or Firm* — James A. Jubinsky

(57) ABSTRACT

This invention relates to novel and useful toluene and styrene derived telomer distributions, such distributions being desirable substrates for the preparation of brominated flame retardants.

17 Claims, No Drawings

(56) References Cited

U.S. PATENT DOCUMENTS

| | | | |
|---|---|---|---|
| 4,829,135 A | 5/1989 | Gunesin et al. |
| 4,853,440 A | 8/1989 | Roggero et al. |
| 4,883,846 A | 11/1989 | Moore et al. |
| 4,950,721 A | 8/1990 | Dias et al. |
| 4,975,496 A | 12/1990 | Tigner et al. |
| 5,112,897 A | 5/1992 | Dever et al. |
| 5,112,898 A | 5/1992 | Dever et al. |
| 5,196,622 A | 3/1993 | Pettijohn et al. |
| 5,198,594 A | 3/1993 | Lillwitz et al. |
| 5,302,768 A | 4/1994 | Hussain |
| 5,310,858 A | 5/1994 | Greiner et al. |
| 5,326,836 A | 7/1994 | Hwang et al. |
| 5,457,248 A | 10/1995 | Mack et al. |
| 5,625,017 A | 4/1997 | Morita et al. |
| 5,637,650 A | 6/1997 | Gill et al. |
| 5,654,384 A | 8/1997 | Halasa et al. |
| 5,677,390 A | 10/1997 | Dadgar et al. |
| 5,686,538 A | 11/1997 | Balhoff et al. |
| 5,687,090 A | 11/1997 | Chen et al. |
| 5,728,782 A | 3/1998 | Brady et al. |
| 5,741,949 A | 4/1998 | Mack |
| 5,767,203 A | 6/1998 | Ao et al. |
| 5,852,131 A | 12/1998 | Balhoff et al. |
| 5,852,132 A | 12/1998 | Dadgar et al. |
| 5,902,865 A | 5/1999 | Gausepohl et al. |
| 5,916,978 A | 6/1999 | Ao et al. |
| 6,008,283 A | 12/1999 | Rose et al. |
| 6,025,450 A | 2/2000 | Lawson et al. |
| 6,093,211 A | 7/2000 | Hamielec et al. |
| 6,133,381 A | 10/2000 | Reed et al. |
| 6,207,765 B1 | 3/2001 | Ao et al. |
| 6,232,393 B1 | 5/2001 | Dadgar et al. |
| 6,232,408 B1 | 5/2001 | Dadgar et al. |
| 6,235,831 B1 | 5/2001 | Reed et al. |
| 6,235,844 B1 | 5/2001 | Dadgar et al. |
| 6,313,230 B1 | 11/2001 | Tsai et al. |
| 6,326,439 B1 | 12/2001 | Dadgar et al. |
| 6,348,166 B1 | 2/2002 | Knoll et al. |
| 6,355,194 B1 | 3/2002 | Agur et al. |
| 6,362,293 B1 | 3/2002 | Newman et al. |
| 6,521,714 B2 | 2/2003 | Kolich et al. |
| 6,657,028 B1 | 12/2003 | Aplin et al. |
| 6,759,498 B2 | 7/2004 | Ikematsu et al. |
| 6,767,960 B2 | 7/2004 | Bae et al. |
| 6,933,343 B2 | 8/2005 | Ikematsu et al. |
| 7,288,612 B2 | 10/2007 | Desbois et al. |
| 7,351,777 B2 | 4/2008 | Moore et al. |
| 7,425,290 B2 | 9/2008 | Semen |
| 7,632,893 B2 | 12/2009 | Kolich et al. |
| 2002/0035214 A1 | 3/2002 | Gill et al. |
| 2002/0183465 A1 | 12/2002 | Babcock et al. |
| 2005/0143526 A1 | 6/2005 | Faust et al. |
| 2005/0209408 A1 | 9/2005 | Lee et al. |
| 2006/0079644 A1 | 4/2006 | Meyer et al. |
| 2007/0004870 A1* | 1/2007 | Kolich et al. ............ 525/333.3 |
| 2007/0142566 A1 | 6/2007 | Kolich et al. |
| 2007/0185280 A1 | 8/2007 | Luther |
| 2007/0232759 A1 | 10/2007 | Chun et al. |
| 2010/0184941 A1 | 7/2010 | Layman, Jr. et al. |

FOREIGN PATENT DOCUMENTS

| | | |
|---|---|---|
| EP | 0741147 A1 | 11/1996 |
| EP | 0775719 A2 | 5/1997 |
| EP | 0806437 A1 | 11/1997 |
| GB | 1107898 | 3/1968 |
| GB | 1174845 | 12/1969 |
| GB | 1270318 | 4/1972 |
| GB | 1342101 | 12/1973 |
| GB | 1536762 | 12/1978 |
| GB | 1589700 | 5/1981 |
| GB | 2164051 A1 | 3/1986 |
| JP | 59-155454 | 9/1984 |
| JP | 62-042938 A | 2/1987 |
| JP | 08-188622 | 7/1996 |
| JP | 09-249705 A1 | 9/1997 |
| JP | 09-249706 A1 | 9/1997 |
| JP | 10-182730 A1 | 7/1998 |
| JP | 11-043511 A1 | 2/1999 |
| JP | 11-080220 A1 | 3/1999 |
| JP | 11-116613 A1 | 4/1999 |
| JP | 2001-341246 A1 | 12/2001 |
| WO | 90/15095 A1 | 12/1990 |
| WO | 99/25746 A1 | 5/1999 |
| WO | 99/55770 A1 | 11/1999 |
| WO | 00/15678 A1 | 3/2000 |
| WO | 02/072645 A1 | 9/2002 |
| WO | 03/020826 A1 | 3/2003 |
| WO | 2005/118245 A1 | 12/2005 |
| WO | 2007/005233 A1 | 1/2007 |
| WO | 2007/076369 A1 | 7/2007 |
| WO | 2008/011477 A1 | 1/2008 |
| WO | 2008/066970 A1 | 6/2008 |
| WO | 2008/154453 A1 | 12/2008 |
| WO | 2008/154454 A1 | 12/2008 |
| WO | 2009/148464 A1 | 12/2009 |
| WO | 2010/065462 A1 | 6/2010 |
| WO | 2010/065464 A1 | 6/2010 |
| WO | 2010/065467 A1 | 6/2010 |
| WO | 2010/065468 A1 | 6/2010 |
| WO | 2010/127072 A1 | 11/2010 |
| WO | 2010/127087 A1 | 11/2010 |
| WO | 2010/127091 A1 | 11/2010 |

OTHER PUBLICATIONS

Patterman, S. P., et al., "Pi Complexation in Ion Pair Bonding. The Structure of Benzyllithium Triethylenediamine", J. Am. Chem. Soc., 1970, 92:5, pp. 1150-1157.

Pines, H., et al., "Sodium-catalyzed side chain aralkylation of alkylbenzenes with Styrene", J. Am. Chem. Soc, 1958, vol. 80(22), pp. 6001-6004.

Pines, H., et al., "Sodium Catalyzed Reactions. II. Side-chain Ethylation of Alkyl Aromatic Hydrocarbons Catalyzed by Sodium", J. Am. Chem. Soc., 1955, vol. 77(3), pp. 554-559.

Reed, J. N., "Product Subclass 13: Benzyllithium Compounds and (Lithiomethyl)Hetarenes", Science of Synthesis, 2006 (vol. date 2005), vol. 8A, pp. 329-355.

Seki, A., et al., "Crossed aldol reaction using cross-linked polymer-bound lithium dialkylamide", Tetrahedron, 2004, vol. 60, pp. 5001-5011.

Sorenson, W. R., et al., Preparative Methods of Polymer Chemistry, Interscience Publishers, Inc., 1961, pp. 198-200.

Strohmann, C., et al., "A Highly Diastereomerically Enriched Benzyllithium Compound: The Molecular Structure and the Stereochemical Course of Its Transformations", Organometallics, 2002, vol. 21, pp. 3079-3081.

Tsukahara, Y., et al., "Preparation and Characterization of alpha-benzyl-omega-vinylbenzyl Polystyrene Macromonomer", Polymer Journal, 1994, vol. 26, No. 9, pp. 1013-1018.

CAPLUS Abstract of Waack, R., et al., "Effects of lithium halides on the reactivity of organolithium compounds (in polymerization)", Chemistry & Industry, 1964, vol. 12, pp. 496-497. 1 page.

Waack, R., et al., "Reactivities of Organolithium Compounds in Tetrahydrofuran. I. As Vinyl Polymerization Initiators", J. Org. Chem., 1967, 32(11), pp. 3395-3399.

Wilhelm, D., et al., "Reactions of Polyanions Derived from Alkylbenzenes", J. Am. Chem. Soc., 1984, 106, pp. 361-367.

Advanced Organic Chemistry, Reactions, Mechanisms, and Structure, 4th Ed., Jerry March, J. Wiley & Sons, 1992, pp. 743-744.

Atkins, Physical Chemistry, P. W., 4th Ed., W. H. Freeman and Co., 1990, p. 800.

Baskaran, D., et al., "Effect of Chelation of the Lithium Cation on the Anionic Polymerization of Methyl Methacrylate Using Organolithium Initiators", Macromolecules, 1995, 28, pp. 7315-7317.

Bildmann, U. J., et al., "Synthesis and Structure of the Tmeda Adduct of a Dibenzyl Lithiate Anion Containing Four-Coordinate Lithium", Organometallics, 2001, 20, pp. 1689-1691.

(56) References Cited

OTHER PUBLICATIONS

CAPLUS Abstract of Chakrapani, S., et al., "Strategies for the controlled, living anionic polymerization of acrylic and methacrylic monomers and novel star polymers", Polymer Science, 1994, vol. 1, pp. 112-117. 1 page.

Concise, Polymeric Materials Encyclopedia, Editor-in-Chief, Joseph C. Salamone, CRC Press, 1999, pp. 1305-1307.

Eberhardt, G. G., et al., "A Catalytic Telomerization Reaction of Ethylene with Aromatic Hydrocarbons", J. Org. Chem., vol. 29, 1964, pp. 2928-2932.

Eberhardt, G. G., et al., "Telomerization Reactions Involving a N-Chelated Organo Lithium Catalyst", Polymer Preprints, 1972, vol. 13, pp. 667-671.

Feil, F., et al., "Benzyl Complexes of the Heavier Alkaline-Earth Metals: The First Crystal Structure of a Dibenzylstrontium Complex", Organometallics, 2001, vol. 20, pp. 4616-4622.

CAPLUS Abstract of Fujimoto, T., et al., "Preparation of monodisperse polystyrenes with high molecular weights", Polymer Journal, 1975, 7(3), pp. 397-401. 1 page.

Gatzke, A.L., "Chain Transfer in Anionic Polymerization. Determination of Chain-Transfer Constants by Using Carbon-14-Labeled Chain Transfer Agents", Journal of Polymer Science, Part A-1, 1969, vol. 7, pp. 2281-2292.

Science Direct Abstract of Helary, G., et al., "Etude de la polymerisation anionique du styrene en milieu non polaire, en presence de N,N,N',N' tetramethyl ethylene diamine", European Polymer Journal, 1978, vol. 14, issue 5, pp. 345-348. 1 page.

Hennion, G. F., et al., "The Polybromination of Alkylbenzenes", J. Am. Chem. Soc., 1946, vol. 68, issue 3, pp. 424-426.

CAPLUS Abstract of Ito, M., et al., "Synthesis of well-defined block copolymers containing poly(N-isopropylacrylamide) segment by anionic block copolymerization of N-methoxymethyl-N-isopropylacrylamide", Designed Monomers and Polymers, 2004, 7(1-2), pp. 11-24. 1 page.

Junkui, C., "Synthesis of Narrow Distribution Polystyrene in RLi-Ligand Complex Systems", Chemical Journal of Chinese Universities, 1989, vol. 10, No. 12, pp. 1246-1250. Abstract only translated.

CAPLUS Abstract of Kalnins, K., et al., "Electronic structure of complexes of benzyl anion and ion pairs with styrene", Vysokimolekulyarnye Soedineniya, Seriya A (1990), 32(2), 316-21. 1 page.

Lamneck, Jr., J. H., "Bromination of the Two Propylbenzenes and Three Butylbenzenes", J. Am. Chem. Soc., 1954, vol. 76, issue 4, pp. 1106-1107.

CAPLUS Abstract of Langer, A. W., Jr., "Reactions of Chelated Organolithium Compounds", Transactions of the New York Academy of Sciences, 1965, 27(7), pp. 741-747. 1 page.

Marechal, Jean-Marc, et al., "Stereoregulation in the anionic polymerization of styrene initiated by superbases", Polymer, 2003, vol. 44, pp. 7601-7607.

Marechal, Jean-Marc, et al., "Stereospecific anionic polymerization of styrene initiated by R2Mg/ROMt 'ate' complexes", Polymer, 2004, 45, pp. 4641-4646.

Maruoka, K., et al., "Novel Anionic Oligomerization by a New, Sequential Generation of Organolithium Compounds", Macromolecules, 1996, 29, pp. 3328-3329.

Milner, R., et al., "Anionic telomerization of butadiene with toluene and diphenylmethane: microstructure and molecular weight", Polymer, vol. 26, 1985, pp. 1265-1267.

Mizuno, T., et al., "Second and Third Virial Coefficients of Polystyrene with Benzyl Ends near the Theta Point", Macromolecules, 2005, 38, pp. 4432-4437.

\* cited by examiner

US 8,642,821 B2

BROMINATION OF TELOMER MIXTURES DERIVED FROM TOLUENE AND STYRENE

REFERENCE TO RELATED APPLICATIONS

This application is the National Stage of International Patent Appl. No. PCT/US09/066127 filed on Nov. 30, 2009, which in turn claims the benefit of U.S. Provisional Patent Appl. No. 61/119,276, filed on Dec. 2, 2008, the disclosures of which are incorporated herein by reference.

TECHNICAL FIELD

This invention relates to a novel process for the production of brominated mixtures of toluene and styrene derived telomers, which brominated mixtures are suitable as flame retardants for use in thermoplastic substrates. The process yields a flame retardant product having a high aromatic bromine content, a low thermally labile bromine content and good color.

BACKGROUND OF THE INVENTION

High aromatic bromine content is a beneficial quality as it portends enhanced flame retardancy per unit weight of flame retardant. However, a high aromatic bromine content can be accompanied by a higher than desired thermally labile bromine content. The thermally labile bromine content of a brominated flame retardant is determined by measurement of the HBr off-gas generated when the flame retardant is heated to a specific elevated temperature, say 300° C., for a specific period of time. The thermally labile bromine content is dependent on the flame retardant's content of HBr by-product still entrapped in the flame retardant (even after finishing steps to reduce this content) and the amount of molecular, non-aromatic bromine present. An example of non-aromatic bromine are alkyl bromides, wherein the alkyl group is either a bridging group between aromatic groups or is an alkyl substituent on an aromatic group. No matter the source, HBr off-gas from the flame retardant used in the thermoplastic formulations can result in damage to molding equipment used to mold (at elevated temperatures) the thermoplastic formulations into articles, e.g. TV enclosures, etc. Although methods exist for removing HBr by-product entrapped in the flame retardant, the chemically bonded, molecular non-aromatic bromide, is more problematic. There are few options open to the practitioner in this latter case as the techniques used for entrapped HBr reduction are of minimal use against the much more stubborn non-aromatic bromine.

Certain brominated polystyrenes (HP 7010 and HP 3010 flame retardants; Albemarle Corporation) are accepted as commercially significant flame retardants for use in a variety of thermoplastics because of their high aromatic bromine content, low thermally labile bromine content and effectiveness. These commercial products exhibit a thermally labile bromine content of less than about 500 ppm while still providing up to about 68 wt % aromatic bromine in the product.

It would be advantageous if a way could be found of providing relatively low molecular weight, non-polymeric brominated aromatic flame retardants having even higher bromine contents than HP 7010 and HP 3010 flame retardants while at the same time exhibiting thermally labile bromine contents comparable to those achieved in the case of perbrominated diphenylalkanes flame retardants, such as decabromodiphenylethane, and also desirable UV characteristics when compounded with UV stabilizers. It would be particularly advantageous if these results could be achieved along with the provision of a non-polymeric flame retardant having desirable color properties.

This invention is believed to enable the achievement of some, if not all, of these advantages.

SUMMARY OF THE INVENTION

This invention relates to processes for producing a brominated flame retardant composition, the process comprising brominating a feed comprising an anionic, chain transfer derived toluene and styrene telomer distribution in the presence of a catalytic quantity of $AlBr_3$ and a solvent.

The processes of this invention can additionally feature the telomer distribution being fed as a solute in proximity to and contemporaneously with joint or separate feed(s) of the brominating agent and the $AlBr_3$. These feeds are made to a reactor pre-charged with solvent or a heel from a previous run, and such feeds, along with pre-charged solvent, at least partially forming a crude reaction mass comprising: (i) the brominated telomer distribution; (ii) by-products/impurities; (iii) solvent; (iv) $AlBr_3$ and; (v), optionally, un-reacted brominating agent. The feeds are made subsurface of the reaction mass level. The reaction mass has a temperature within the range of from about −20° C. to about 5° C. The bromination reaction is fast. The resultant crude product (reaction mass) is removed from the reactor for downstream finishing.

N-bromoamines are likely to be present in the crude product. These amines are derived from the chain transfer telomerization promoter, e.g., N,N,N',N'-tetramethylethylenediamine (TMEDA) that accompanies the telomer distribution feed from the production of the telomer. The N-bromoamines can lead to color bodies that, if not removed or reduced, can give the final brominated flame retardant a poor color.

After the bromination, the crude reaction mass is preferably quenched in water to deactivate the $AlBr_3$ catalyst, such quenching forming an aqueous phase and an organic slurry phase. The phases are then separated and optionally, either additional water washes are conducted, or bromine is distilled from the organic slurry.

A preferred feature of the processes of this invention comprises, subsequent to the separation of the phases, washing the separated organic phase, or any other organic phase derived therefrom, with a basic, aqueous $NaBH_4$ solution to reduce the content of the N-bromoamine color bodies and HBr that may still be present, such washing(s) occurring at a temperature within the range of from about 36° to about 65° C. When using a bromination solvent that forms an azeotrope with water with a boiling point below about 50° C., it is desirable to conduct the treatment under superatmospheric pressure so that pot temperatures in the range of 50° C. to 65° C. can be achieved in the condensed phase. Note: It has been found that in the presence of significant quantities of active bromine species, a violent reaction may occur when the organic slurry is contacted with the basic aqueous $NaBH_4$ solution. Therefore, one should ensure that the presence of bromine species be at a minimum such as by use of additional water extractions or distillation. Subsequent to the $NaBH_4$ treatment, the organic slurry has a relatively high pH because of the tendency of the slurry to retain residual portion of the basic aqueous wash. Therefore, additional fresh water washes are employed to reduce the pH level of the slurry, as evidenced by the pH of the separated water wash.

The product slurry is best isolated by feeding the slurry to a well-stirred vessel containing fresh water at a temperature in the range of about 60° C. to about 98° C., depending on the azeotropic boiling point of the bromination solvent with water. In conducting this operation, the separated organic slurry phase is fed to a vessel containing the aqueous medium while concurrently removing the bromination solvent by distillation or azeotropic distillation, including any distillable impurities that may be present. Because the solids or the solid material can contain occluded bromine, it is desirable to introduce a small amount (e.g., less than 0.1 wt % of the total aqueous phase) of $NaBH_4$ into the aqueous precipitation medium to destroy any active bromine species that may be released during isolation process. Irrespective of the temperature at which the precipitation is conducted, it is best to finish the procedure by heating to about 98° C. to help remove any bromine occluded in the solids. The solids are removed by any conventional solid-liquid separation procedure such as filtration, centrifugation, decantation, or the like. The resulting wet cake is dried and, if need be, roasted in an oven at 130° C. to 180° C. under a nitrogen purge stream.

In the following "Detailed Description of the Invention" further description is given for processes of this invention. The process features to which the description applies, in part or in whole, are within the scope of the inventions disclosed herein.

FURTHER DETAILED DESCRIPTION OF THE INVENTION

The Telomer Distribution Feed

The telomer distributions that are suitable feeds for bromination in accordance with the processes of this invention are characterized by one or more of:

(a) a distribution of molecules of the formula

wherein each Ar is a phenyl group, for each molecule in the distribution, "n" is a whole number in the range of 0 to 6, and wherein,
(i) at least about 46 GPC area % of the molecules have an "n" value equaling 0,
(ii) about 1 to about 26 GPC area % of the molecules have an "n" value equaling 1, and
(iii) 0 to about 14 GPC area % of the molecules have an "n" value equaling 2;

(b) a distribution of molecules of the formula

wherein each Ar is a phenyl group, for each molecule in the distribution, "n" is a whole number in the range of 0 to 6, and wherein the distribution is characterized by a majority of the molecules in the distribution having an "n" value of 0 and a minority, not exceeding 49 GPC area %, of the molecules in the distribution having an "n" value of 1, 2, 3, 4, 5 or 6 wherein the GPC area % for "n" equals 1>"n" equals 2>"n" equals 3>"n" equals 4>"n" equals 5>"n" equals 6;

(c) a non-polymeric and non-oligomeric distribution of molecules of the formula

 (b)

wherein each Ar is a phenyl group, and, for each molecule in the distribution, "n" is a whole number in the range of 0 to 6 and wherein the distribution includes molecules having "n" values from 1 to 6.

Preferred telomer mixtures have telomer distributions as presented above with reference to the formula, which distributions are characterized by having a content of from about 46 to about 76 GPC area % for molecules having "n"=0; from about 16 to about 26 GPC area % for molecules having "n"=1; and from about 1 to about 14 GPC area % for molecules having "n"=2.

Further preferred telomer mixtures have telomer distributions as presented above with reference to the formula, which distributions are characterized by having a content of (i) from about 76 to about 95 GPC area % of the molecules having an "n" value equaling 0, (ii) from about 17 to about 5 GPC area % of the molecules having an "n" value equaling 1, and (iii) from about 5 to 0 GPC area % of the molecules having an "n" value equaling 2.

Still further preferred telomer mixtures have telomer distributions as presented above with reference to the formula, which distributions are characterized by having a content of (i) from about 95 to about 99 GPC area % of the molecules having an "n" value equaling 0, and (ii) from about 5 to about 1 GPC area % of the molecules having an "n" value equaling 1.

While, the GPC area % for molecules having an "n" value of 0, 1, and 2, or 0 and 1 are recited above that is not to mean that no other molecules having an "n" value outside of 0 to 2 or 0 to 1 can be present. Rather, the characterization of the feeds by only reciting the GPC area % for molecules of the population, "n"=0 to 2, or 0 to 1 highlights the importance of this limited population and the higher GPC area % numbers associated therewith. See, Examples 1-7 wherein products produced fall within the foregoing characterization, but also have populations of molecules, though not large, having "n" values greater than 2 or 1.

As can be seen from the above, the telomer distributions used in the bromination processes of this invention favor molecular populations in which the "n" value range is low as compared to oligomeric distributions, in which the "n" value range is from 7 to 25 and as compared to polymeric distributions in which the "n" value range is from 26 to 80. There are two benefits realized by using telomer mixtures in which "n" is from 0 to 6. First, obtaining a very high Br wt % is facilitated for the above described telomer distributions as the proportion of penta-brominatable aromatic end groups to tetra-brominatable interior aromatic groups is inherently larger for the telomer distributions of this invention than it is for oligomeric or polymeric distributions. Thus, the brominated flame retardants of this invention can have very high aromatic bromine contents, exceeding 72 wt % of bromine, and easily reaching over 78 wt % of bromine.

Secondly, the telomer distributions of this invention present fewer sites for the formation of non-aromatic bromine, a thermally labile species, than is the case for higher molecular weight polystyrenes produced by conventional polymerization techniques, e.g. free-radical, anionic, etc.

As used above, the term "non-polymeric" is to be taken in the context of the OECD definition of "polymer".

"A chemical substance consisting of molecules characterized by the sequence of one or more types of monomer units and comprising a simple weight majority of molecules containing at least three monomer units which are covalently bound to at least one other monomer unit or other reactant and which consists of less than a simple weight majority of molecules of the same molecular weight. Such molecules must be distributed over a range of molecular weights wherein differences in the molecular weight are primarily attributable to differences in the number of monomer units."

The telomer distribution feeds used in the processes of this invention can be obtained by the anionic addition of 1 to about 7 styrene units to toluene using catalytic quantities of lithium reagents complexed with poly(tertiary amines). The telomer process features the use of toluene as both reactant and as reaction solvent. More, specifically, the process is effected by adding styrene to toluene in the presence of catalytic quantities of alkyllithium (preferably butyllithium) and TMEDA. The reaction mass temperature should be within the range of from about 77° C. to about 115° C. during the addition. This addition reaction is an anionic, chain transfer telomerization reaction. Further details on the anionic, chain transfer telomerization reaction that can be used to make the telomer distribution feeds used in the processes of this invention can be found in commonly-owned International Publication Number WO 2010/065462, claiming the benefit of a U.S. Provisional Application entitled "Toluene and Styrene Derived Telomer Distributions, filed Dec. 2, 2008, all disclosure of which Provisional Application is enclosed herein], which International Publication is incorporated herein by reference as if fully set forth.

Examples 1-7 illustrate methods for obtaining telomer distributions that are suitable for feeds to the processes of this invention.

EXAMPLE 1

A dry 500-mL 4-necked, oil-jacketed glass flask was equipped with a thermocouple, glass overhead stirrer with glass paddle, condenser and $N_2$ inlet. The reactor was charged with 150 mL (130.5 g, 1.55 mol) anhydrous toluene and then subsequently with 2.7 mL (0.0054 mol) n-butyllithium (2M in cyclohexane) and 0.72 mL (0.56 g, 0.0048 mole) TMEDA at ambient temperature. The temperature of the reaction mixture was increased to 110° C. Styrene (50 mL, 45 g, 0.43 mol) was pumped into the reactor at over 137 minutes at a constant rate while maintaining constant and significant agitation of the mixture. Upon completion of the styrene feed, 20 mL anhydrous toluene was pumped into the reaction mixture to clear the feed line of styrene. The reaction mixture was then cooled to 80° C. and then quenched with 0.5 mL isopropyl alcohol. After cooling to room temperature and settling of the lithium isopropoxide salts, the reactor was sampled for GPC analysis. The GPC area % analysis excluding unreacted toluene was as follows: $C_{15}H_{16}$ 64.3%; $C_{23}H_{24}$ 23.4%; $C_{31}H_{32}$ 8.2%; $C_{39}H_{40}$ 2.9%; $C_{47}H_{48}$ 0.9%; $C_{55}H_{56}$ 0.3%; $C_{63}H_{64}$ 0%; $C_{71}H_{72}$ 0%; $C_{79}H_{80}$ 0%; $C_{87}H_{88}$ and higher oligomers 0%.

EXAMPLE 2

The procedure of Example 1 was used except that 45 g (0.43 mole) of styrene was fed over 127 minute period to a reaction mass formed from 130.5 g (1.55 mole) anhydrous toluene, 1.8 mL (0.0036 mole) 2 M n-butyl lithium and 0.42 g (0.0036 mole) of TMEDA. The GPC area % analysis excluding unreacted toluene was as follows: $C_{15}H_{16}$ 46.1%; $C_{23}H_{24}$ 25.5%; $C_{31}H_{32}$ 13.6%; $C_{39}H_{40}$ 7.2%; $C_{47}H_{48}$ 3.8%; $C_{55}H_{56}$ 1.7%; $C_{63}H_{64}$ and higher oligomers 2%.

EXAMPLE 3

The procedure of Example 1 was used except that 60.9 g (0.58 mole) of styrene was fed over 173 minute period to a reaction mass formed from 115.0 g (1.25 mole) anhydrous toluene, 2.4 mL (0.00487 mole) 2 M n-butyl lithium and 0.57 g (0.00487 mole) of TMEDA. The GPC area % analysis excluding unreacted toluene was as follows: $C_{15}H_{16}$ 64.8%; $C_{23}H_{24}$ 22.3%; $C_{31}H_{32}$ 7.6%; $C_{39}H_{40}$ 3.0%; $C_{47}H_{48}$ 1.9%.

EXAMPLE 4

Reactor System

A spherical glass 12-liter creased reactor with oil jacket was equipped with a reflux condenser, distillation head, submerged thermocouple, bottom drain valve, and stainless steel internal cooling coils. Temperature was tightly maintained at a set point via PID controller that regulates water flow to the cooling coils. Vigorous agitation was accomplished by means of an overhead stirring assembly comprised of a 19 mm OD glass shaft with two sets of glass impellers, one set pitched and the other flat, fused to the shaft. The reactor is essentially free of all wetted PTFE parts or other polymeric fluorinated materials or elastomers.

Feeding Techniques

The reactor was maintained under an inert dry $N_2$ atmosphere during all operations. The reactor was charged with the chain transfer agent(s) through a dip leg by means of a diaphragm pump. Alkyl lithium, additional solvents and the amine promoter TMEDA were all fed subsurface to the stirred chain transfer agent(s) through the same dip leg. Styrene was pumped into the reactor by means of a metering pump through a 3" cylindrical column (1.75" dia.≈100 g) of Basic Aluminum Oxide (EMD Chemicals, Aluminum oxide 90, mesh 70-230, column chromatography grade) and delivered as a fine stream or spray above the surface of the reaction mixture through two 1/16" OD feed nozzles.

Detailed Procedure

Toluene 2913 g, (3.4 liters, 31.61 mol) was charged to the reactor previously heated to 115° C. The toluene is refluxed and azeotropically dried over a 4 hour period; Karl Fischer moisture analysis indicated 21 ppm of residual $H_2O$, this toluene was dried with 1.5 g of n-BuLi solution. The dried toluene was cooled to 82° C. with the oil jacket and PID controller operating the coiling coils both set at that temperature. Upon cooling to the set point temperature, 63 g n-BuLi solution (2M in cyclohexane, 0.162 mol) was charged through the dip leg below the surface of the gently agitated (300 rpm) toluene reaction mixture. The feed line was then flushed with 75 mL of anhydrous toluene. Next, 46.4 g of TMEDA (0.399 mol) was charged to the reactor through the subsurface feed line forming the characteristic bright red color of TMEDA-complexed benzyl lithium anion with concomitant off-gassing of butane. The subsurface line was flushed with a second 75 mL aliquot of anhydrous toluene via the metering pump. Reactor agitation was increased to 510 rpm and 1713 g of styrene (99+%, 16.45 mol) dissolved in 3070 g of toluene were fed over 360 minutes. The well-calibrated metering pump was programmed to feed at a constant rate of 13.3 g/min. Anhydrous cyclohexane (2×200 mL) was charged to the styrene feed system to flush the alumina bed. The styrene feed to the reactor was deemed complete when no further heat of reaction was observed generally signified by the closing of the automated control valve on the cooling coils. The set point of PID temperature controller was maintained at 82° C. and water was fed through the cooling coils as needed while the flow of the hot oil was altered to bypass the reactor jacket. The reaction mixture was quenched at 75° C. with a 50 mL aliquot of deoxygenated water resulting in a water-white turbid mixture. The reaction mixture was washed with deoxygenated water (3×650 mL). Phase cuts were rapid and required little settling time. Water and any rag or emulsion was removed through the bottom drain valve. During the course of the 6-hour feed, an aliquot was removed after 3 hours for analysis. The GPC area % analysis (excluding unreacted toluene) was as follows: $M_n$=226, $M_w$=247 $M_z$=281, PD=1.091 $C_{15}H_{16}$ 70.3%; $C_{23}H_{24}$ 20.1%; $C_{31}H_{32}$ 6.4%; and higher oligomers 3.2%. The temperature of the oil jacket was increased to 130° C. while the control valve to the cooling coils turned off. Cyclohexane, residual moisture and toluene are distilled through a simple distillation head (1 atm.) until a pot temperature of 114° C. was observed. An aliquot was removed for analysis via GPC, the composition of the reaction product mixture (a telomer distribution of this invention) was as follows: $C_{15}H_{16}$ 75.7%; $C_{23}H_{24}$ 17.4%; $C_{31}H_{32}$ 4.7%; and higher telomers 2.2%.

It will thus be seen that the isolated telomer distribution of this invention formed in this Example 4 was composed of 1,3-diphenylpropane (75.7 GPC area %), 1,3,5-triphenylpentane (17.4 GPC area %), 1,3,5,7-tetraphenylheptane (4.7 GPC area %), and 2.2 GPC area % of higher telomer(s), which presumably was mainly or entirely 1,3,5,7,9-pentaphenylnonane. Its GPC profile was as follows: $M_n$=219, $M_w$=238 $M_z$=269, PD=1.087.

EXAMPLE 5

A dry 500-mL 4-necked, oil-jacketed glass flask was equipped with a thermocouple, glass overhead stirrer with glass paddle, condenser and nitrogen inlet. The reactor was charged with 175 mL (151.4 g, 1.64 mol) of anhydrous toluene and then subsequently with 2.24 g (0.0082 mol) of n-butyl lithium (23.5 wt % in cyclohexane) and 2.97 mL (2.29 g, 0.0197 mol) of TMEDA at ambient temperature. The temperature of the reaction mixture was increased to 85° C. Styrene (94.6 mL, 86 g, 0.83 mol) and toluene (175 mL 151.4 g, 1.64 mol) were mixed and pumped into the reactor at over 359 minutes at a constant rate while maintaining constant and significant agitation of the mixture at a temperature of 85° C. Upon completion of the styrene feed, 20 mL anhydrous toluene was pumped into the reaction mixture to clear the feed line of styrene. The reaction mixture was then cooled to 80° C. and then quenched with 0.5 mL of isopropyl alcohol. After cooling to room temperature and settling of the lithium isopropoxide salts, the reactor was sampled for GPC analysis. The GPC area % analysis (excluding unreacted toluene) of this reaction product mixture was as follows: $M_n$=203, $M_w$=210 $M_z$=220, PD=1.033 with $C_{15}H_{16}$ 86.3%; $C_{23}H_{24}$ 11.9%; $C_{31}H_{32}$ 1.8%; and higher oligomers 0%.

It will thus be seen that the unisolated telomer distribution of this invention formed in this Example 5 was composed of 1,3-diphenylpropane (86.3 GPC area %), 1,3,5-triphenylpentane (11.9 GPC area %), and 1,3,5,7-tetraphenylheptane (1.8 GPC area %).

EXAMPLE 6

A dry 500-mL 4-necked, oil-jacketed glass flask was equipped with a thermal couple, glass overhead stirrer with glass paddle, condenser and $N_2$ inlet. The reactor was charged with 150 mL (130.5 g, 1.55 mol) of anhydrous toluene and then subsequently with 2.7 mL (0.0054 mol) of n-butyl lithium (2 M in cyclohexane) and 2.42 mL (1.88 g, 0.0162 mole) of TMEDA at ambient temperature. The temperature of the reaction mixture was increased to 110° C. Styrene (50 mL, 45 g, 0.43 mol) dissolved in 150 mL of toluene was pumped into the reactor over a period of 56 minutes at a constant rate while maintaining constant and significant agitation of the mixture with the temperature held at 110-115° C. Upon completion of the styrene feed, 20 mL anhydrous toluene was pumped into the reaction mixture to clear the feed line of styrene. The reaction mixture was then cooled to 80° C. and then quenched with 0.5 mL isopropyl alcohol. After cooling to room temperature and settling of the lithium isopropoxide salts, the reactor was sampled for GPC analysis. The GPC area % analysis excluding unreacted toluene was as follows: $M_n$=214, $M_w$=225 $M_z$=243, PD=1.054 $C_{15}H_{16}$ 84.5%; $C_{23}H_{24}$ 13.1%; $C_{31}H_{32}$ 2.3%; $C_{39}H_{40}$ 0.2% and higher oligomers 0%.

It will thus be seen that the unisolated telomer distribution of this invention formed in this Example 6 was composed of 1,3-diphenylpropane (84.5 GPC area %), 1,3,5-triphenylpentane (13.1 GPC area %), 1,3,5,7-tetraphenylheptane (2.3 GPC area %), and 1,3,5,7,9-pentaphenylnonane (0.2 GPC area %).

EXAMPLE 7

A glass-lined, 100-gallon jacketed reactor equipped with an overhead condenser, submerged thermal well/thermal couple and a bottom drain valve. Temperature was maintained at a set point by controlling the temperature of the water flowing through the jacket using a steam control valve. Vigorous agitation was accomplished by means of a three-blade, retreat-curve agitator on a variable speed drive. The reactor is essentially free of all wetted PTFE parts or other polymeric fluorinated materials or elastomers.

The reactor was maintained under an inert dry $N_2$ atmosphere during all operations. The reactor was charged with the chain transfer agent(s) through a dip leg by means of pressure transfer from a portable tank. Alkyl lithium, additional solvents and the amine promoter (TMEDA) were all fed subsurface to the stirred chain transfer agent(s) through the same dip leg. Styrene was pressure transferred from a portable, pressure vessel by means of a metering valve through a 24" cylindrical column (3" dia.≈6 lbs.) of 3 Å mol sieves (Zeochem) and delivered as a fine stream or spray above the surface of the reaction mixture through a slit feed nozzle.

Toluene 140 pounds, (689 mol) was charged to the reactor; Karl Fischer moisture analysis indicated 7 ppm residual $H_2O$. Agitation began. The solvent was heated to 78° C. by applying tempered water to the vessel jacket. Upon reaching the set point temperature, 4.07 pounds of TMEDA (15.9 mol) in 10 pounds of toluene (49.24 mol) was charged to the reactor through the dip leg below the surface of the agitated toluene reaction mixture. The feed line was then flushed with 21 pounds (103 mol) of anhydrous toluene. Next, 3.9 lb n-BuLi solution (23.5 wt % in cyclohexane) (6.53 mol n-BuLi) was charged through the subsurface feed line forming the characteristic bright red-orange color of TMEDA complexed benzyl lithium anion with concomitant off gassing of butane. The feed line was then flushed with 21 pounds (103 mol) of anhydrous toluene. 374.4 lb of styrene (99+%, 1629 mol, American Styrenics) were fed over 162 minutes. The styrene was added by means of pressure transfer from a nitrogen regulated portable tank through a metering valve at a constant feed rate of 2.3 lb/min. The reactor was allowed to ride for 5 minutes to make certain the reaction was complete.

The reaction mixture was quenched at 70° C. with 10 gallons of 0.75 wt % ammonium chloride solution which had been deoxygenated overnight. The reaction mixture was washed with a second 10 gallons of deoxygenated water. Phase cuts were rapid and required little settling time. Water and any rag or emulsion was removed through the bottom drain valve.

The reactor was heated to atmospheric boiling point using tempered water on the vessel jacket. Steam was then applied to the reactor jacket to increase the temperature of the reactor jacket to 140° C. Cyclohexane, residual moisture and toluene boiled, condensed in the overhead condenser, and drained to a drum until a pot temperature of 135° C. was observed. The reactor was cooled to 50° C. Vacuum was applied to the vessel and the reactor was heated to boiling point. Steam was then applied to the reactor jacket to increase the temperature of the reactor jacket to 140° C. Vacuum was used to decrease the reactor pressure to 35 mm Hg. Cyclohexane, residual moisture and toluene boiled, condensed in the overhead condenser, and drained to a drum until a pot temperature of 135° C. was observed. An aliquot was removed from the reactor for analysis via GPC ($M_p$: 301, $M_n$: 433, $M_w$: 626, $M_z$: 883, PD: 1.45). The reaction mass (443 lbs) was collected in a 350-gallon tote bin.

A 3893 g sample of the crude plant-stripped reaction mixture was stripped using a wiped film evaporator (WFE) via continuous operation of residual toluene and 1,3-diphenylpropane (to 1.0 GPC area % max specification) to yield 3111 g of a product that had the following GPC analysis: $M_p$: 409, $M_n$: 543, $M_w$: 698, $M_z$: 907, PD: 1.29. WFE operating conditions were as follows: feed rate=1.33 L/hr, oil jacket temperature=155° C., Pressure=<0.1 mmHg and condenser temperature=0° C. Additionally the cold finger condensed 784 g of a mixture having the following GPC analysis: $M_n$=204, $M_w$=212, PD=1.04 with $C_{15}H_{16}$ 80.65%; $C_{23}H_{24}$ 17.7%; $C_{31}H_{32}$ 1.5%; and $C_{39}H_{40}$ 0.2%.

It will thus be seen that this condensate, a telomer distribution of this invention, was composed of 1,3-diphenylpropane (80.65 GPC area %), 1,3,5-triphenylpentane (17.7 GPC area %), 1,3,5,7-tetraphenylheptane (1.5 GPC area %), and 1,3,5,7,9-pentaphenylnonane (0.2 GPC area %).

The GPC area % values set forth in Examples 1 through 7 were obtained by GPC (described in more detail below) using an oligopore column which provided baseline to baseline resolution of the individual telomers as well as partially resolved any accompanying short chain oligomers. It is therefore possible to discuss these product mixtures in terms of the relative formation of discrete molecules. The resulting data demonstrates that a variety of mixtures of telomers can be prepared under different process conditions. The product distributions demonstrate a dependence on the ratio of monomer to chain transfer agent, on the ratio of monomer to the tertiary polyamine complex organolithium initiator, and on the feed rate of the monomer.

Table 1 summarizes the conditions and results for Examples 1-7.

A general description of a bromination procedure used in the practice of this invention is as follows:

Preparation for Bromination

Dichloromethane (DCM) or other suitable bromination solvent was dried (5-40 ppm moisture by Karl Fisher) with activated alumina of Acidic Aluminum Oxide (EMD Chemicals, Aluminum oxide, mesh 70-230, column chromatography grade). All feed lines, feed tanks and glassware were dried (oven dried at 130° C. min 2 hour where appropriate) and purged over-night prior to use in the bromination reaction. All glassware, feed lines, and feed tanks are maintained under a $N_2$ atmosphere during the course of the set-up and the operation of the bromination reactor.

The amount of $AlBr_3$ catalyst (commercially available) needed to make a 0.25 mole % (calculated using the formula [moles $AlBr_3$/moles $Br_2$]*100%=0.25 mole % $AlBr_3$) solution of active catalyst was weighed and then transferred to oven dried reagent bottles in a nitrogen-purged glove box. By active catalyst, it is meant that amount of catalyst above any additional amount that would be otherwise deactivated by moisture either in the bromine itself or any other process stream involved in the bromination reaction. Bromine (5-10 ppm moisture content) was pumped into the reagent bottle containing the $AlBr_3$ and then stirred with a PTFE coated magnetic stirring bar for 30 minutes to assure homogeneous dissolution of the catalyst. The 0.25 mole % $AlBr_3$ in bromine solution was then transferred to a graduated feeding vessel placed on a large capacity laboratory balance.

The anionic chain-transfer styrene telomer (ACTST) used was dissolved in dry (5-10 ppm moisture) DCM to make a

TABLE 1

| Example | 1 | 2 | 3 | 4 | 5 | 6 | 7 |
|---|---|---|---|---|---|---|---|
| Styrene/Toluene (vol/vol) | 0.33 | 0.33 | 0.5 | 0.26 | 0.27 | 0.16 | n/a |
| TMEDA/Butyllithium (mol/mol) | 1 | 1 | 1 | 2.46 | 2.4 | 3.0 | n/a |
| Styrene/butyllithium (mol/mol) | 80 | 120 | 120 | 101 | 101 | 80 | n/a |
| Time of Styrene Feed (min) | 137 | 127 | 173 | 360 | 360 | 56 | n/a |
| Temperature (° C.) | 110-115 | 110-115 | 110-115 | 82 | 85 | 110-115 | |

| Product | | GPC | GPC | GPC | GPC | GPC | GPC | GPC |
|---|---|---|---|---|---|---|---|---|
| n = | MW | Formula | area % | area % | area % | area % | area % | area % | area % |
| 0 | 196.29 | $C_{15}H_{16}$ | 64.3 | 46.1 | 64.8 | 75.7 | 86.3 | 84.5 | 80.7 |
| 1 | 300.44 | $C_{23}H_{24}$ | 23.4 | 25.5 | 22.3 | 17.4 | 11.9 | 13.1 | 17.7 |
| 2 | 404.59 | $C_{31}H_{32}$ | 8.2 | 13.6 | 7.6 | 4.7 | 1.8 | 2.3 | 1.5 |
| 3 | 508.74 | $C_{39}H_{40}$ | 2.9 | 7.2 | 3 | 2.2 | | 0.2 | 0.2 |
| 4 | 612.89 | $C_{47}H_{48}$ | 0.9 | 3.8 | 1.9 | | | | |
| 5 | 717.04 | $C_{55}H_{56}$ | 0.3 | 1.7 | | | | | |
| 6+ | 821.19 | $C_{63}H_{64}$ | | 2 | | | | | |

BROMINATION

In the practice of this invention, any known method for bromination of aromatic hydrocarbons may be employed. In general, the brominations are conducted in the absence of light and preferably use elemental bromine as the brominating agent. The bromination is carried out under anhydrous conditions, using a suitable Lewis acid catalyst such as an aluminum halide or ferric halide catalyst. To minimize bromination on aliphatic carbon atoms, the reaction is preferably conducted at temperatures below about 25° C. A bromination solvent such as, for example, dibromomethane, ethylene dibromide, bromochloromethane, dichloromethane, ethylene dichloride is typically used in the process.

25-wt % solution. The solution was then charged to a graduated feeding vessel. The 0.25 mole % $AlBr_3$ in bromine and the 25 wt % ACTST in DCM solution are co-fed via separate peristaltic pumps through 1/8" (3.2 mm) O.D. feed lines to a well-stirred fresh or recycle heel of anhydrous DCM at 0° C. to −10° C. The relative feed rates are constantly monitored such that ratio of the two reagents fed remains constant or near constant during the course of the electrophilic bromination reaction.

Bromination Equipment Set-Up:

A 5 L oil jacketed flask (bromination reactor) was equipped with an overhead glass stirrer shaft, PTFE stirring paddle, a water-cooled condenser, thermowell, nitrogen inlet, and bottom drain valve. The reactor was vented through a calcium sulfate moisture trap to a well-stirred caustic scrubber to absorb co-product HBr and entrained $Br_2$. Additionally the reactor was outfitted with three inlet lines: 1) ¼" (6.4 mm) O.D. PTFE BCM feed for initial feed of BCM to the reactor (the BCM can be either fresh or a BCM recycle heel from a previous run); 2) ⅛" (3.2 mm) O.D. substrate/BCM subsurface feed line; and 3) ⅛" (3.2 mm) O.D. $Br_2/AlBr_3$ subsurface feed line. The $AlBr_3/Br_2$ and ACTST/BCM feed lines are secured such that both inlet lines discharge their contents in close proximity creating a locally high reagent concentration. The bromination reactor was completely covered with aluminum foil to exclude light and the reaction was conducted in a darkened ventilation hood.

The bromination reactor was placed above a 6-liter water quench pot with a ⅜" (9.5 mm) O.D. PTFE drain line that connects the bottom drain valve of the bromination reactor to the quench pot to allow for direct transfer of the bromination reactor's contents. The quench pot was oil jacketed and equipped with an over-head stiffing mechanism, thermowell and was baffled for intimate mixing of organic and aqueous phases. The quench pot had a nitrogen inlet and was purged to a caustic scrubber. The quench pot had a bottom drain valve to enable transfer of the pot's contents to an intermediate 5 liter storage vessel.

The intermediate storage vessel was piped to transfer its contents to a wash kettle. The wash kettle was a 6-liter oil-jacketed, baffled reactor outfitted with an over-head stirrer, thermocouple and bottom drain valve.

Product isolation set-up provides a water-containing vessel into which the product slurry is fed accompanied by the concomitant azeotropic removal of DCM. The precipitate from is passed through an oven for drying.

EXAMPLE 8

Bromination

To the 5 L bromination reactor described above was charged 3320.23 g (4.4 liters) of dry DCM (33 ppm moisture, Karl Fisher). The DCM was cooled in the dark to −1° C. and a previously prepared 25 wt % solution comprised of 200 g of the condensate of Example 7 (which was composed of $C_{15}H_{16}$ 80.65%; $C_{23}H_{24}$ 17.7%; $C_{31}H_{32}$ 1.5%; and $C_{39}H_{40}$ 0.2%) and 399.3 g of dry DCM was charged to a dry, 2000 mL $N_2$ blanketed graduated cylinder outfitted with a ⅛" (3.2 mm) PTFE feed line placed to transfer the entire content of the cylinder by means of a peristaltic metering pump to the bromination reactor. The previously prepared $AlBr_3$ (0.25 mol %) in bromine (1600 g) was transferred via a peristaltic pump into a 1.5 liter graduated cylinder. This feed vessel was maintained under a $N_2$ atmosphere and was outfitted with a ⅛" (3.2 mm) PTFE feed line placed to transfer the desired amount of bromine solution by means of a peristaltic metering pump to the bromination reactor.

The two reagents are co-fed at predetermine relative rates such that the entire content of the two feeds are charged and simultaneously completed in 120 minutes. Ample cooling was provided through out the operation such that the reaction temperature remains close to −2° C. Upon completion of the feed the reaction was allowed to stir for an additional 60 minutes and gradually warmed to 15° C. to allow unreacted bromine to be consumed. The reaction mixture was transferred (gravity) to the 6 L quench pot through the bottom drain valve and the ⅜" (9.5 mm) O.D. PTFE transfer line.

The quench pot was previously charged with 1000 mL tap water (25° C.) and stirred at 400 rpm to assure intimate mixing of the organic and aqueous phase. The quench was exothermic and a 10° C. temperature rise was observed. Agitation was slowed to 20 rpm and the organic slurry phase allowed to settle. The red bromine/HBr aqueous phase gradually separated forming the top layer. The lower organic slurry phase was transferred to a 5 L storage vessel containing 1000 mL of 10% NaOH.

This two-phase system was then transferred to the 6 L wash kettle and refluxed (39° C.) for 30 minutes. Agitation was interrupted and the bottom organic layer cut from the reactor. The organic layer was returned to the completely drained kettle and washed twice with 1000 mL of tap water until a pH of 10 was observed and the color of the water wash was faint yellow. The organic slurry was then washed with 0.5 wt % sodium borohydride in 2 wt % NaOH at 36° C. The organic slurry was separated and washed a final time with 1000 mL of tap water.

The slurry was placed in a stirred tank and gravity fed to the precipitation reactor (10 liters tap water containing 2 grams $NaHBH_4$, 60° C.) with concomitant azeotropic distillation of DCM. Upon completion of the feed the pot temperature was increased to 98° C. and held at that temperature for 20 minutes. The resulting off white product was collected by vacuum filtration rinsed with tap water until the rinse registered a pH<9. The product dried in a nitrogen purged oven at 185° C. to a constant weight, 850 g. The product thus obtained had the analyses shown in Table 2.

TABLE 2

| Bromination Example | | BR-8 |
|---|---|---|
| Wt % Br XRF | | 78.09 |
| Thermal HBr 280° C. (ppm) | | 202 |
| Thermal HBr 300° C. (ppm) | | 540 |
| DSC (° C.) | $T_g$ | 180 |
| | M.P. min (° C.) | 225.67 |
| TGA (° C.) | 1% wt Loss | 259.87 |
| | 5% wt Loss | 322.48 |
| | 10% wt Loss | 342.07 |
| | 50% wt Loss | 390.83 |
| ASTM D 1925 | L | 88.33 |
| | a | 0.12 |
| | b | 4.86 |
| | YI | 9.92 |

Further details concerning the bromination processes of this invention are set forth below.

The Bromination Solvent

The solvent used in forming the telomer distribution solution and the reactor pre-charge can be selected from any of the following exemplary solvents; dichloromethane, dibromomethane, bromochloromethane, bromotrichloromethane, chloroform, 1,2-dibromoethane, 1,1-dibromoethane, 1-bromo-2-chloroethane, 1,2-dichloroethane, 1,1,2-tribromoethane, 1,1,2,2-tetrabromoethane, 1,2-dibromopropane, 1-bromo-3-chloropropane, 1-bromobutane, 2-bromobutane, 2-bromo-2-methylpropane, 1-bromopentane, 1,5-dibromopentane, 1-bromo-2-methylbutane, 1-bromohexane, 1-bromoheptane, bromocyclohexane, and liquid isomers, homologs, or analogs thereof and mixtures of any two or more of the foregoing. Preferred solvents are dichloromethane, dibromomethane, and 1,2-dichloroethane. Dichloromethane is a particularly preferred solvent.

Whatever the solvent chosen is, it is important to insure that it is relatively free of water. Water in the reaction system during bromination will affect catalytic activity of the $AlBr_3$ as is well recognized in the art. Generally, it is best that the solvent contain less than about 50 ppm (weight/weight) water. In regard to water, all reactants should be dry. The brominating agent, e.g. bromine, should not contain more than about 30 ppm water. The telomer distribution feed should also be sufficiently dry so as to not introduce deleterious amounts of water into the bromination.

The amount of solvent in the telomer distribution solution feed is that amount which at least enables the formation of a free-flowing, low viscosity solution. In cases where the telomer distribution is already a low-viscosity liquid, consideration for using a solvent-free telomer distribution feed can be given. However, if has been found that the use of a solvent is preferred as it helps dilute the telomer distribution feed so that efficient bromination can occur in the reaction mass. Generally, when the solvent is dichloromethane, from about 40 to about 80 wt % of the solution will be solvent. Preferred amounts of solvent are 65 to about 75 wt %.

The pre-charge of solvent to the reactor prior to the reactant and catalysts feeds is that amount which will provide a sufficient mass to provide an adequate heat sink to disperse the heat of the bromination reaction combined with the heat of solution of the by-product HBr so that a "heat kick" or temperature spike is minimized in the proximity of the above mentioned feeds. To this end, it is also preferred that the crude reactor contents/crude reaction mass be stirred to promote thermal and mass uniformity therein. In addition, the pre-charge of solvent to the reactor should be sufficient to keep the reaction mixture, which is predominately in the form of a slurry, in a sufficiently fluid condition so as to minimize the extent to which solids adhere to the interior surfaces of the reactor and to facilitate its transfer to another vessel upon completion of the bromination reaction.

AlBr$_3$ Catalyst

The AlBr$_3$ can be fed as a solute or a slurry in a bromination solvent or diluent separate from the brominating agent feed. However, such a separated feeding scheme is not preferred. Process convenience dictates that the brominating agent be bromine and that the AlBr$_3$ and the bromine be fed as a single feed. AlBr$_3$ readily dissolves in bromine. The amount of AlBr$_3$ fed, whether separately or in combination with the bromine feed, is a catalytic amount sufficient to provide from about 0.3 to about 1 mole % AlBr$_3$ per mole of bromine fed.

$$\text{Mole \% AlBr}_3 = (\text{weight of AlBr}_3/266.7 \div \text{weight of Bromine}/159.81) \times 100.$$

Brominating Agent

The amount of bromine fed is that amount required to achieve the desired bromination level sought assuming some small loss of brominating agent overhead with by-product HBr. Thus, for example, obtaining a 68 wt % bromine containing composition, about 2.8 moles of Br$^+$ are fed per mole of phenyl group present in a given a telomer distribution, while, when desiring to obtain a 72 wt % bromine content, about 3.3 moles of Br$^+$ are fed per mole of phenyl group present. When obtaining very high bromine contents, say about 78 wt % bromine, about 4.5 moles of Br$^+$ fed per mole of phenyl group present. When obtaining very high bromine contents, say about 80 wt % bromine, about 4.9 moles of Br$^+$ fed per mole of phenyl group present.

The preferred brominating agent is Br$_2$ which provides one mole of Br$^+$ per mole of Br$_2$. Other brominating agents are premixed or preformed bromine chloride, or bromine chloride that is formed in situ. However, neither is preferred in that the aluminum tribromide does not remain as a solute when added to bromine chloride. Instead, it tends to separate by exchange reaction to form insoluble aluminum trichloride.

For the preferred brominating agent, bromine, conveniently, one can simply charge bromine based on the equations below (this ignores the small mass of the unbrominated telomer distribution lost due to substitution of the protons by bromine and thus results in a slight over charge of bromine, enough to compensate for bromine lost overhead with HBr). In the following, "telomer distribution"="telomer."

$$\text{wt Br} = \text{wt \% Br} \cdot \text{wt telomer}_{brominated} \quad \text{a)}$$

$$\text{wt}_{brominated} \approx \text{wt telomer}_{unbrominated}/(1-\text{wt \% Br}) \quad \text{b)}$$

Note: In b), the approximation is the result of ignoring the small amount of mass not accounted for the protons substituted by bromine.

Thus, $$\text{wt Br} \approx \text{wt \% Br} \cdot [\text{wt telomer}_{unbrominated}/(1-\text{wt \% Br})] \quad \text{c) and}$$

$$\text{Moles bromine} = 2 \cdot \text{wt Br}/159.81 \quad \text{d)}$$

$$\text{Moles bromine} \approx 2 \cdot \text{wt \% Br} \cdot [\text{wt telomer}_{unbrominated}/(1-\text{wt \% Br})]/159.81 \quad \text{e)}$$

It is preferred to feed, as close as is possible, just the amount of bromine needed to obtain the wt % bromine desired. If, excess bromine is fed, then at least some of that excess will be in the crude reaction mass and will have to be removed in down-stream finishing steps. However, not using excess bromine feed becomes problematic when the practitioner is seeking a very high bromine content composition; say from about 74 to about 80 wt % bromine. To obtain such compositions an excess of from about 0.05% to about 2% bromine is used to provide the most favorable reaction kinetics as is practical.

Whatever the reason for the presence of excess bromine in the crude reaction mass, conventional techniques recognized in the art to remove such excess bromine can be used, e.g. using a reducing agent, e.g., sodium sulfite, to convert the bromine to water soluble bromide salts. However, it has been observed that the use such reducing agents tends to encourage the formation of an emulsion and/or rag during some of the down-stream finishing steps. Such, emulsion or rag layer causes separation difficulties and process inefficiencies. It is a feature of this invention that these emulsions and rag layers can be easily handled by the use of surfactants, e.g. sodium dodecyl sulfate, to minimize the emulsions and rag layers, all as hereinafter described. However, all such problems are avoided if sulfite and/or bisulfite and likely thiosulfate reducing agents are not used. Use of multiple water extraction or distillation by conventional means of excess bromine in lieu of use of such sulfur-containing reducing agents is the recommended procedure for use pursuant to this invention. Other reducing agents such as hydrazine can be employed but are not recommended due to regulatory toxicity issues.

The telomer distribution solution, brominating agent and AlBr$_3$ feeds should be made beneath the surface of the reactor contents/reaction mass and in close proximity to each other. It is a principle of this invention that the bromination of the telomer distribution should occur quickly. The rates of reaction for the brominations of this invention are very fast due to reaction kinetics. Thus, in the processes of this invention, the rate-determining factor is the rate of mass transfer. Hence, the use of proximate feeds is utilized so that the reactants and catalyst are close, to each other. Another factor in assuring fast bromination is the feed of the AlBr$_3$ in solution with bromine. It is believed that the bromine preconditions the AlBr$_3$ to the active catalyst state so that the catalyst is active when first fed. One technique to insure close proximity of the feeds is to provide that the feed tubes into the reactor contents/reaction mass be held together so that they discharge in adjacent parallel or in direct, impinging directions.

Having the feeds discharge beneath the reactor content/crude reaction mass liquid levels is beneficial as it ensures that there is heat dissipation away from the feeding area. Having a "hot spot" at the feeding area is to be avoided to the extent commercially possible. Again, stirring of the reactor contents/crude reaction mass also aids in heat dispersion.

The amount of solvent pre-charge to the reactor should be that amount necessary to accomplish the heat dissipation function without burdening the process with higher than needed material handling expenses.

The feed rate of the individual feeds should be as high as is possible considering the reactor size and design, the heat that must be handled and the cooling available to assist in heat management, the feeding apparatus available and the ability to safely handle HBr byproduct gas. The higher the possible feed rates, the more efficient the process.

During the co-feed, the reactor contents/crude reaction mass should be kept at a temperature within the range of from about −20° C. to about 5° C. and preferably within the range of from about −7° C. to about 0° C. The feeds to the reactor are conveniently fed at about ambient temperature, say 25° C. To obtain the reactor contents/crude reaction mass temperatures mentioned above, the reactor is provided with adequate cooling. The temperature should be measured as close to the feed area as is practical.

The pressure in the reactor during the bromination is not critical, super-atmospheric pressures being the norm. However, very high pressures are not preferred in the context of equipment requirements and safety issues. Autogenous pressures are permissible.

Subsequent to the reactant and catalyst feeds, it is permissible to allow the reaction mass to experience a ride time to ensure that bromination has ceased. It is permissible, when brominating above 71 wt % bromine, to allow the temperature to warm to about 25° C. to help facilitate consumption and react out as much of the fed bromine as is practical. This is particularly desirable when brominating above 73% and where the practitioner decides to forgo the use of a bromine reducing agent during the initial aqueous quench so as to avoid any emulsion and rag layer difficulties. When producing highly brominated telomer distributions, the ride times will be longer than if lower brominated products are sought. Generally, ride times of 15 minutes to 60 minutes are suitable.

After the feeds are completed and the ride time, if any, has passed, the crude reaction mass is removed from the reactor and quenched in water. The quench is conveniently performed at ambient temperature and generally speaking no heating other than the heat of solution of residual HBr is needed to effect a phase separation. Since bromine and other active brominating species can be present it is preferred to minimize heating of the mixture and to limit exposure to visible light. This assists, to some extent, in helping to ensure a low thermally labile bromine content. Use of multiple water extraction or distillation by conventional means is used to remove excess bromine. As mentioned previously, if the crude reaction mass or, for that matter, any organic phase that is treated down-stream of the bromination, contains unreacted bromine, such bromine content can be lowered or eliminated by the use of the reducing agent, $NaBH_4$, in a later wash step.

The water quench does not have a ride time as the purpose of the water quench is to deactivate the $AlBr_3$. Once the quench is complete, two defined phases are formed, an aqueous phase and an organic slurry phase. The organic slurry phase contains solvent and the brominated telomer distribution, and will require further treatment. To initiate treatment, the organic phase is separated from the aqueous phase.

After the water quench and phase separation and any additional bromine removal steps (water extraction or distillation) are complete, it is a preferred feature of this invention to wash the organic slurry phase with a basic sodium borohydride solution. The borohydride and its borane by-products act to convert available active bromine species, including available unreacted brominating agent, e.g. bromine (if any should still be present), and any available derivatives formed from the unreacted brominating agent (e.g., hypobromites, and/or hypobromous acid) and also any available N-bromoamines, so that the bromine and active bromine species are reduced to bromide, and in the case of the N-bromides, this material is reduced to sodium bromide and free amine. The use of sodium borohydride to reduce bromine in the production of brominated polystyrenes is known. However, a novel feature of the preferred processes of this invention is the use of a caustic solution of sodium borohydride to reduce the amount of N-bromo amine derived color bodies that accompany the brominated telomer distribution. Thus, for the processes of this invention the sodium borohydride has a primary function, i.e., to reduce the amount of N-bromoamines present, and a secondary function, i.e., the reduction of any amount of bromine present. Thus, quantitatively, the amount of sodium borohydride used is that amount necessary to handle both functions. As used in this paragraph, the term "available", as used in connection with active bromine species, unreacted brominating agent, derivatives formed from the unreacted brominating agent, and N-bromoamines, denotes that the identified materials are not occluded within solids to such an extent that they cannot be removed simply by contact with the sodium borohydride solution.

As the caustic aqueous sodium borohydride solution is used to treat the organic phase, an aqueous phase is formed. The pH of the sodium borohydride solution is such that the formed aqueous phase has a pH between about 10 and about 14 throughout the period that the formed aqueous phase is in contact with the organic phase.

The preferred sodium borohydride content of the treating solution is within the range of from about 0.05 to about 0.5 wt % sodium borohydride, based on the total weight of the treating solution.

An important feature of the caustic sodium borohydride step is that a temperature above about 36° C. and preferably within the range of from about 50° C. to about 65° C. at one atmosphere is maintained during the treatment period. Again, superatmospheric pressures can be used for bromination solvents that form azeotropic mixtures with water having boiling points below 50° C., such that the preferred pot temperature range can be attained.

The sodium borohydride treatment temperature is maintained for at least that amount of time needed to obtain the benefits of the treatment, generally a convenient time of 30 minute period is deemed to be sufficient, and shorter periods may indeed be sufficient, especially when conducting this step and/or all of the steps prior to this step involving bromination as a continuous process. The practitioner can choose a lesser amount or a greater amount of time as suits his/her needs.

The use of the above described aqueous caustic sodium borohydride treatment or wash can be used at any time after the water quench step and phase separation and on any recovered organic phase in the down stream, finishing sequence.

After the final washing, the organic slurry phase is separated from the aqueous phase and fed to hot water, say from about 60° C. to about 98° C., depending upon the identity(ies) of the organic bromination solvent(s) used, to flash off the solvent present and to yield solids in the aqueous phase. As mentioned above, it is best to finish the process at a temperature of about 98° C. to help remove occluded bromine that may be present in the solids. Additionally, such temperatures are needed to ensure the complete removal of higher boiling halogenated solvent components resulting from halogen exchange reactions between chlorinated hydrocarbons or chlorobromohydrocarbons with evolved HBr. Once the solvent has been flashed off, the solids are separated from the water by conventional means, e.g. filtration and the like. The separated solids are then dried by exposure to elevated temperatures (e.g., 135° C. to 185° C.) under an inert atmosphere purge (e.g., a nitrogen purge) to a constant weight to ensure removal of bromine occluded in the solids. If the particle size are such that they are too coarse to be used in flame retardant compositions, it may be necessary to grind the solids prior to drying. Whether or not subjected to grinding or other forms of comminution, the dried solids are the finished brominated telomeric flame retardant compositions of this invention.

Analytical Procedures

Known analytical methods can be used or adapted for use in assaying the characteristics of the compositions and formulations of this invention.

GPC wt % Telomer Distributions

The GPC area % values were obtained by GPC using a modular system with a Shimadzu autosampler (model SIL-9), a Shimadzu refractive index detector (model RID-6A), a Waters HPLC pump (model 510) and a Waters TCM column heater. The columns used were Polymer Labs (Varian) Oligopore columns, 300 mm by 7.5 mm, part number 1113-6520. The solvent used was tetrahydrofuran, HPLC grade. The test procedure used entailed dissolving approximately 0.10 g of sample in 10 mL of THF. An aliquot of this solution is filtered and 50 µL is injected on the columns. Based on isolated 1,3-diphenylpropane and 1,3,5-triphenylpentane adducts, and the mode of separation is size exclusion, peaks are identified according to their order of elution as 1,3-diphenylpropane, 1,3,5-triphenylpentane, 1,3,5,7-tetraphenylheptane, 1,3,5,7,9-pentaphenylnonane, etc. The individual peaks of the oligomeric material are then assigned theoretical molecular weight values. A calibration curve is constructed using these theoretical values and their corresponding retention times. Based on this calibration, the overall distribution data is calculated and reported. The calculations were performed by the Viscotek Omnisec, version 4.2.0.237 gel permeation chromatography (GPC) data collection and processing system.

Total Bromine Content (Combustion)

Bromine content of the brominated products produced from the telomers of this invention is typically determined by use of a combustion method. The procedure of this method is as follows:

A 0.04-0.08 g of sample of the Brominated Telomer is weighed on a 0.00001 g accuracy, onto ¼ sheet of creased black filter paper on a 5 place analytical balance. The sample is folded inside the filter paper placed in a platinum sample holder. A combustion flask is prepared by adding 15 mL of caustic aresenite solution and 3 drops concentrated $NH_4OH$. The flask is thoroughly flushed for at least two minutes with oxygen. The platinum sample holder is placed in the top of the combustion flask which is then flushed for at least one more minute. The flask is stoppered and secured so that the flask is gas tight when inverted. Silicone grease is used to form a continuous seal around the entire joint surface. The inverted combustion flask containing the sample is placed into a Thomas-Ogg oxygen flask infrared igniter. The sample is ignited and the residue is dissolved in deionized water made basic with solid KOH and further digested by boiling. The solution is concentrated, cooled and acidified with sulfuric acid. Bromide is then titrated with a 0.1 to 0.01 N $AgNO_3$ standardized solution using a silver titrode on a autotitrator. Wt % Bromine of the brominated telomer is given by the equation below:

$$\text{wt \% Br} = \frac{(S-B)(N)(7.9904)}{\text{Sample Weight in Grams}}$$

where:
S=milliliters of $AgNO_3$ required to titrate the sample
B=milliliters of $AgNO_3$ required to titrate the blank
N=normality of $AgNO_3$ Yellowness Index Hunter Colorimeter In order to assess the color properties of the brominated products formed from the telomers of this invention, the analytical procedure described in ASTM D 1925 was employed.

Thermogravimetric Analysis

Thermogravimetric analysis (TGA) is also used to test the thermal behavior of the flame retardant compositions formed from the telomers of this invention. The TGA values are obtained by use of a TA Instruments Thermogravimetric Analyzer. Each sample is heated on a Pt pan from 25° C. to about 600° C. at 10° C./min with a nitrogen flow of 50-60 mL/min.

Thermal Stability Test (Thermally Labile Bromine Test

This test procedure for determining the thermal stability of the brominated flame retardants produced by bromination of the telomers of this invention is a procedure essentially as described in U.S. Pat. No. 5,637,650. In conducting this test, each sample is run in duplicate. A 2.00 g+/–0.01 g sample is placed into a new clean 20 mm by 150 mm test tube. With a neoprene stopper and Viton® fluoroelastomer tubing, the test tube is connected to a nitrogen purge line with exit gas from the test tube being passed successively through subsurface gas dispersion frits in three 250-mL sidearm filter flasks each containing 200 mL of 0.1 N NaOH and 5 drops of phenolphthalein. With a constant nitrogen purge at 0.5 SCFH, the test tube is heated at 300° C. in a molten salt bath (51.3% $KNO_3$/48.7% $NaNO_3$) for 15 minutes followed by 5 minutes at ambient temperature. The test tube containing the sample is then replaced with a clean dry test tube, and the apparatus is purged with nitrogen for an additional 10 minutes with the empty test tube in the 300° C. salt bath. The test tube, tubing and gas dispersion tubes are all rinsed with deionized water, and the rinse is combined quantitatively with the solutions in the three collection flasks. The combined solution is acidified with 1:1 $HNO_3$ and titrated with 0.01 N $AgNO_3$ using an automatic potentiometric titrator (Metrohm 670, 716, 736, or equivalent). Results are calculated as ppm HBr: HBr=(mL $AgNO_3$ to end point)·(normality of $AgNO_3$) (80912)/(sample wt.). The tubing is thoroughly dried with nitrogen before the next analysis. Each day before the first sample, three empty clean test tubes are run as blanks to assure there is no residual hydrogen halide in the system.

The brominated telomer distributions of this invention may be used as flame retardants in formulations with virtually any flammable material. The material may be macromolecular, for example, a cellulosic material or a polymer. Illustrative polymers are: olefin polymers, cross-linked and otherwise, for example homopolymers of ethylene, propylene, and butylene; copolymers of two or more of such alkene monomers and copolymers of one or more of such alkene monomers and other copolymerizable monomers, for example, ethylene/propylene copolymers, ethylene/ethyl acrylate copolymers and ethylene/propylene copolymers, ethylene/acrylate copolymers and ethylene/vinyl acetate copolymers; polymers of olefinically unsaturated monomers, for example, polystyrene, e.g. high impact polystyrene, and styrene copolymers, polyurethanes; polyamides; polyimides; polycarbonates; polyethers; acrylic resins; polyesters, especially poly(ethyleneterephthalate) and poly(butyleneterephthalate); polyvinyl chloride; thermosets, for example, epoxy resins; elastomers, for example, butadiene/styrene copolymers and butadiene/acrylonitrile copolymers; terpolymers of acrylonitrile, butadiene and styrene; natural rubber; butyl rubber and polysiloxanes. The polymer may be, where appropriate, cross-linked by chemical means or by irradiation. The brominated telomeric distributions of this invention can also be used in textile applications, such as in latex-based back coatings.

The amount of brominated telomeric distributions of this invention used in a formulation will be that quantity needed to obtain the flame retardancy sought. In general, the formulation and resultant product may contain from about 1 to about 30 wt %, preferably from about 5 to about 25 wt % of a brominated telomeric distribution of this invention. Master batches of polymer containing a brominated telomeric distribution, which are blended with additional amounts of substrate polymer or binding agent, typically contain even higher concentrations of the flame retardant, e.g., up to 95 wt % or more.

It is advantageous to use the brominated telomeric distributions of this invention in combination with antimony-based synergists, e.g. $Sb_2O_3$. Such use is conventionally practiced in most, if not all, flame retardant applications in which aromatic bromine flame retardants are used. Generally, the flame retardant products of this invention will be used with the antimony based synergists in a weight ratio ranging from about 1:1 to 7:1, and preferably of from about 2:1 to about 4:1.

Any of several conventional additives used in thermoplastic formulations may be used, in their respective conventional amounts, with the brominated telomeric distributions of this invention, e.g., plasticizers, antioxidants, fillers, pigments, UV stabilizers, etc.

Thermoplastic articles formed from formulations containing a thermoplastic polymer and a brominated telomeric distribution product of this invention can be produced conventionally, e.g., by injection molding, extrusion molding, compression molding, and the like. Blow molding may also be appropriate in certain cases.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Each and every patent or publication referred to in any portion of this specification is incorporated in toto into this disclosure by reference, as if fully set forth herein.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text taken in context clearly indicates otherwise.

The invention may comprise, consist or consist essentially of the materials and/or procedures recited herein.

This invention is susceptible to considerable variation in its practice. Therefore the foregoing description is not intended to limit, and should not be construed as limiting, the invention to the particular exemplifications presented hereinabove.

The invention claimed is:

1. A process for producing a brominated telomer distribution, the process comprising brominating to a bromine content of more than 72 wt %, a telomer distribution characterized by one or more of the following:

(a) a distribution of molecules of the formula

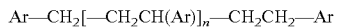

wherein each Ar is a phenyl group, for each molecule in the distribution, "n" is a whole number in the range of 0 to 6, with the telomere distribution comprising less than 2 GPC area % of molecules having an "n" value greater than 6, and wherein,
  (i) at least about 46 GPC area % of the molecules have an "n" value equaling 0,
  (ii) about 1 to about 26 GPC area % of the molecules have an "n" value equaling 1, and
  (iii) 0 to about 14 GPC area % of the molecules have an "n" value equaling 2;

(b) a distribution of molecules of the formula

wherein each Ar is a phenyl group, for each molecule in the distribution, "n" is a whole number in the range of 0 to 6, with the telomer distribution comprising less than 2 GPC area % of molecules having an "n" value greater than 6, and wherein the distribution is characterized by a majority of the molecules in the distribution having an "n" value of 0 and a minority, not exceeding 49 GPC area %, of the molecules in the distribution having an "n" value of 1, 2, 3, 4, 5 or 6 wherein the GPC area % for "n" equals 1>"n" equals 2>"n" equals 3>"n" equals 4>"n" equals 5>"n" equals 6;

(c) a non-polymeric distribution of molecules of the formula

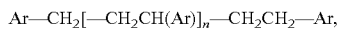

wherein each Ar is a phenyl group, and, for each molecule in the distribution, "n" is a whole number in the range of 0 to 6 with the telomer distribution comprising less than 2 GPC area % of molecules having an "n" value greater than 6, and wherein the distribution includes molecules having "n" values from 1 to 6.

2. A process as in claim 1 wherein said distribution of molecules is characterized by having a content of from about 46 to about 76 GPC area % for molecules having "n"=0; from about 16 to about 26 GPC area % for molecules having "n"=1; and from about 1 to about 14 GPC area % for molecules having "n"=2.

3. A process as in claim 1 wherein said distribution of molecules is characterized by having a content of (i) from about 76 to about 95 GPC area % of the molecules having an "n" value equaling 0, (ii) from about 17 to about 5 GPC area % of the molecules having an "n" value equaling 1, and (iii) from about 5 to 0 GPC area % of the molecules having an "n" value equaling 2.

4. A process as in claim 1 wherein the telomer distribution is fed as a solute in proximity to and contemporaneously with joint or separate feed(s) of bromine as the brominating agent and $AlBr_3$ as the catalyst, such feeds being made to a reactor pre-charged with solvent, and such feeds, along with pre-charged solvent, at least partially forming a reaction mass comprising: (i) the reaction products obtained by the feed of the distribution of molecules and its impurities, brominating agent and $AlBr_3$; (ii) solvent; (iii) $AlBr_3$ and; (iv), optionally, unreacted brominating agent, and such feeds being made subsurface of the reaction mass level and the reaction mass having a temperature within the range of from about $-20°$ C. to about $5°$ C.

5. The process of claim 4 wherein the telomer distribution feed and the joint or separate feeds are impinging feeds.

6. The process of claim 4 wherein the telomer distribution is fed in solution with dichloromethane.

7. The process of claim 4 wherein at least a portion of the brominating agent and $AlBr_3$ are fed jointly as a solution comprising same.

8. The process of claim 4 wherein in A) the brominating agent and the $AlBr_3$ are jointly fed as a solution comprising the two.

9. The process of claim 8 wherein the telomer distribution feed and the joint feed are impinging feeds.

10. The process of claim 4 wherein the bromination occurs at a temperature within the range of from about $-10°$ C. to about $0°$ C.

11. The process of claim 4 wherein the brominating agent is bromine.

12. The process of claim 4 wherein the process further comprises (1) quenching the reaction mass in water to deactivate the $AlBr_3$ catalyst, such quenching forming an aqueous phase and an organic slurry phase and (2) separating the organic slurry phase and the aqueous phase from each other.

13. A process as in claim 12 wherein subsequent to the quenching, the separated organic slurry phase is optionally (i) washed with multiple portions of fresh water, or (ii) distilled to remove as much as possible free bromine, and thereafter is treated with basic, aqueous $NaBH_4$ solution to reduce available active bromine species, including available N-bromoamines, such treatment with basic, aqueous $NaBH_4$ solution occurring at a temperature within the range of from about $36°$ to about $65°$ C.

14. A process as in claim 13 wherein subsequent to the treatment with basic, aqueous $NaBH_4$ solution, the organic slurry phase is separated and water washed until the separated washed water exhibits the pH of less than or equal to 10.

15. A process as in claim 14 wherein the separated organic slurry phase is fed to a vessel containing an aqueous medium optionally containing sodium borohydride in an amount of up to about 0.1 wt %, based on the total weight of the aqueous medium, while concurrently removing the bromination solvent by distillation or azeotropic distillation, including any distillable impurities that may be present.

16. A process as in claim 15 wherein subsequent to precipitation and concurrent azeotropic distillation of solvent, the solid product is isolated by a solids-liquid separation procedure, and optionally ground or comminuted to obtain a desired particle size distribution and then subjecting the solid product to drying to a constant weight under an inert atmosphere and at a temperature in the range of about $135°$ C. to about $185°$ C., said grinding or comminution additionally facilitating removal, during the drying, of occluded bromine that may be present in the solids.

17. The process as in claim 1 wherein the bromination is to a bromine content in the range of about 74 to about 80 wt %.

\* \* \* \* \*

UNITED STATES PATENT AND TRADEMARK OFFICE
CERTIFICATE OF CORRECTION

PATENT NO.         : 8,642,821 B2                          Page 1 of 1
APPLICATION NO.    : 13/130101
DATED              : February 4, 2014
INVENTOR(S)        : William J. Layman, Jr. et al.

It is certified that error appears in the above-identified patent and that said Letters Patent is hereby corrected as shown below:

In the Claims

Column 20, line 27 in Claim 1, reads "telomere", and should read -- telomer --.

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,642,821 B2
APPLICATION NO.  : 13/130101
DATED            : February 4, 2014
INVENTOR(S)      : Layman, Jr. et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this

Twenty-ninth Day of September, 2015

Michelle K. Lee
*Director of the United States Patent and Trademark Office*